United States Patent
Nuthi

(10) Patent No.: US 10,496,954 B2
(45) Date of Patent: Dec. 3, 2019

(54) SYSTEMS AND METHODS FOR MEDICAL TECHNOLOGY DYNAMIC SWARMING TAGS

(71) Applicant: General Electric Company, Schenectady, NY (US)

(72) Inventor: Sridhar Nuthi, Sussex, WI (US)

(73) Assignee: General Electric Company, Schenectady, NY (US)

(*) Notice: Subject to any disclaimer, the term of this patent is extended or adjusted under 35 U.S.C. 154(b) by 18 days.

(21) Appl. No.: 15/857,100

(22) Filed: Dec. 28, 2017

(65) Prior Publication Data
US 2019/0205820 A1 Jul. 4, 2019

(51) Int. Cl.
| G06Q 10/08 | (2012.01) |
| G16H 40/40 | (2018.01) |
| G06K 7/10 | (2006.01) |
| G16H 30/20 | (2018.01) |
| G06K 17/00 | (2006.01) |

(52) U.S. Cl.
CPC ....... *G06Q 10/087* (2013.01); *G06K 7/10297* (2013.01); *G06K 17/0022* (2013.01); *G06Q 10/08* (2013.01); *G16H 30/20* (2018.01); *G16H 40/40* (2018.01); *G06K 2017/009* (2013.01); *G06K 2017/0045* (2013.01); *G06K 2017/0051* (2013.01)

(58) Field of Classification Search
None
See application file for complete search history.

(56) References Cited

U.S. PATENT DOCUMENTS

| 8,713,377 | B2 | 4/2014 | Nuthi | |
| 9,003,514 | B1 | 4/2015 | Nuthi | |
| 2006/0124738 | A1* | 6/2006 | Wang | G06K 7/10079 235/385 |
| 2008/0079578 | A1* | 4/2008 | Kim | H04W 88/02 340/572.1 |
| 2010/0127829 | A1* | 5/2010 | Daneshmand | G06K 7/0008 340/10.1 |
| 2010/0259395 | A1 | 10/2010 | Nuthi | |
| 2011/0071850 | A1 | 3/2011 | Nuthi | |
| 2012/0076371 | A1* | 3/2012 | Caruba | A61B 6/583 382/128 |
| 2012/0158419 | A1 | 6/2012 | Nuthi | |
| 2012/0158428 | A1 | 6/2012 | Nuthi | |
| 2013/0159786 | A1 | 6/2013 | Nuthi | |
| 2013/0160096 | A1 | 6/2013 | Nuthi | |

* cited by examiner

*Primary Examiner* — Kristy A Haupt
(74) *Attorney, Agent, or Firm* — McCoy Russell LLP

(57) ABSTRACT

Methods and systems are provided for dynamic, self-swarming smart tags. In one example, a system includes a plurality of smart tags each configured to be coupled to a respective component of a medical imaging system. Each smart tag of the plurality of smart tags is configured to broadcast identification information usable by other smart tags in order to dynamically form a family, the family formed based on the broadcast identification information matching stored identification information and further based on a proximity of each smart tag of the plurality of smart tags to one another.

20 Claims, 4 Drawing Sheets

SYSTEMS AND METHODS FOR MEDICAL TECHNOLOGY DYNAMIC SWARMING TAGS

FIELD

Embodiments of the subject matter disclosed herein relate to medical technology inventory management, and more particularly, smart tags to facilitate inventory management in a medical environment.

BACKGROUND

Medical technologies, such as medical imaging, may rely on sophisticated equipment that is regularly serviced on-site by field engineers. If a field engineer arrives to perform an on-site service on a piece of medical equipment that includes multiple parts and discovers a lack of inventory of replaceable parts, missing tools, or other issues, service may be delayed, which may delay patient medical care. Further, if degraded parts in the piece of medical equipment are replaced with non-original manufacturer parts, performance of the medical equipment may suffer.

BRIEF DESCRIPTION

In one embodiment, a system includes a plurality of smart tags each configured to be coupled to a respective component of a medical imaging system. Each smart tag of the plurality of smart tags is configured to broadcast identification information usable by other smart tags in order to dynamically form a family, the family formed based on the broadcast identification information matching stored identification information and further based on a proximity of each smart tag of the plurality of smart tags to one another.

In this way, each component of an asset (such as a medical imaging system, or a field engineer tool kit) may include a smart tag. The smart tags may facilitate self-managing of inventory levels (e.g., inventory of a given replaceable part of the tool kit) by dynamically forming families and, with each member of the family acting as a master and slave, raising alerts and initiating workflows without the need for an external monitoring application to do such tasks. The smart tags may form families and broadcast notifications (such as low inventory notifications) without being directed to do so by an external monitoring application.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
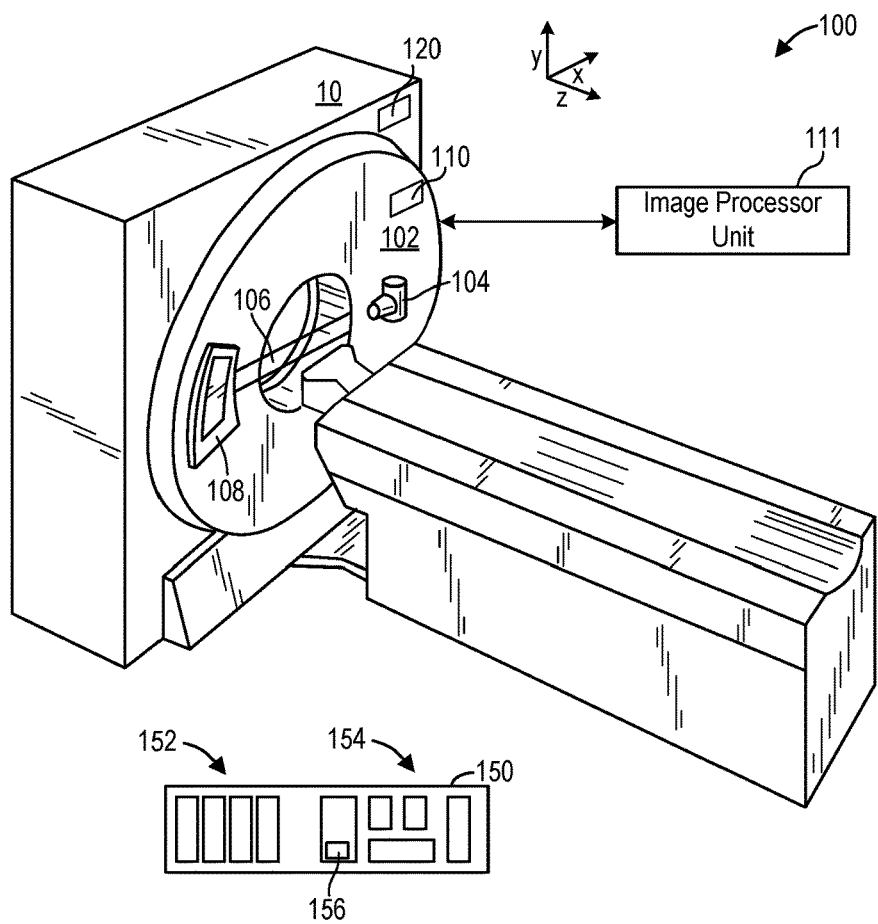
FIG. 1 shows a pictorial view of an example imaging system.

The following description relates to various embodiments of asset and inventory management using dynamic and self-swarming tags. Certain types of equipment, such as medical or laboratory equipment (e.g., medical imaging systems, gas or liquid analyzers), may be serviced on-site by traveling field engineers rather than being sent to a service center. When a field engineer is performing an on-site service of a piece of equipment, various parts of the equipment may be replaced (e.g., due to wear or degradation). Thus, the field engineer may travel with an inventory of replacement parts as well as tools to perform the service. To ensure that the field engineer arrives to perform an on-site service with a tool kit including a sufficient supply of replacement parts and tools, the inventory of the tool kit may be monitored so that missing tools or low inventory replacement parts may be replenished. Typically, monitoring of the inventory may be done by the field engineer (e.g., manually), or automatically using active or passive RFID tags or scan codes and an external application such as an RTLS system or a complex server application that continuously listens for heartbeats and manages the identification of product families and inventory levels. Complex logic has to be written to handle various workflows and each deployment setting may necessitate custom server logic to handle proper management of equipment. Accordingly, such automatic systems may be costly and complex.

Thus, according to embodiments disclosed herein, self-organizing and swarming tags that associate with each other as a family/line of assets may be included in nearly any tool, replacement part, and equipment component in order to facilitate tracking of inventory based on proximity. The concept may be applicable to identical products (such replacement parts) and may also be extended to tools that a field engineer is likely to carry in a tool kit (hammers, drills, etc.), or the tools that engineers may carry along in mobile equipment configurations, such as mobile imaging equipment.

Each tag may include proximity detection circuitry and a built in custom protocol that identifies the tag, its purpose, the asset that it is attached to (such as engineer tool kit, MRI machine, etc.) and the family class it is configured to (tool kit component, MRI machine component, hammer, etc.). The tags may be powered by external energy beams or long life batteries. The tags may broadcast their information using a custom protocol using low bandwidth and low power network protocols such as low power BLUETOOTH® or near-field communication as applicable.

Another feature of the tags is the ability to listen for custom broadcast packets coming over the protocol that the tags are configured to listen to. When tags in the proximity identify themselves, and based on the family classification that the tags are configured to, a dynamic family or swarm may be created. Each member of the swarm may be notified of the number of swarm members. When the number of members of the swarm changes, each member may be notified of the change in swarm number. Each tag may be configured with an event threshold, such that if the number of members in the swarm drops below the threshold, each member may broadcast a notification of the low swarm inventory. The broadcast notification may be sent directly to a listener within the proximity, or the notification may be sent to a central listener in the cloud using standard protocols like REST.

The ability to configure the family classification and associated rules on thresholds and notifications allow for the dynamic tag family to scale for a multitude of real world applications. Additional logic to monitor the health of the tag, battery life, and tag location may be built in to ensure that the tags are easily located and serviced when needed. Given that the dynamic association of tags into a swarm or family happens based proximity of the tags to each other, the tags may be used in cases where an item is disassociated from the current family and associated back into a new family (for example, a part taken from a field engineer inventory and put into a customer asset). In this way, the part may be associated with a first family while in a first location, and then may dissociate from the first family when moved to a second location, where the tag may associate with a second family.

By having the smartness built into the tags, overall inventory management may be simplified. For example, if the entire bill of materials (BOM) or field-replaceable unit (FRU) of an imaging scanner is configured with the dynamic tags disclosed herein, anytime a part is removed from the imaging scanner, a workflow may be triggered (such as assessing if the part is replaced with an approved part) by the dynamic tag family itself. Self-organizing dynamic tags also may monitor a scenario where a part or tool leaves its current location and is moved to a different location. Self-disassociation and association based on the proximity would provide an automatic tally of inventory and ensure reduced loss of inventory (such as when a tool is shared by one field engineer with another field engineer).

Figure 2:
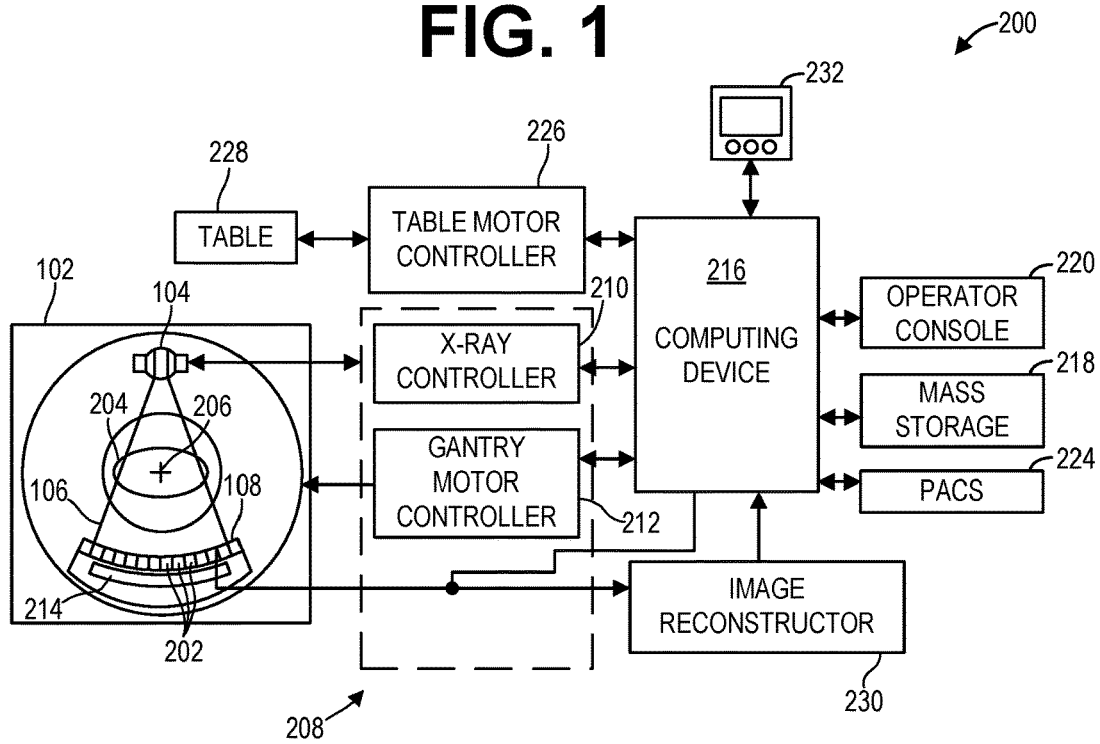
FIG. 2 shows a block schematic diagram of an example imaging system.

As mentioned previously, each component or field-replacement unit of an asset (such as an imaging scanner) may include a smart tag as disclosed herein. FIGS. 1-2 illustrate a CT imaging system that is one such example asset that may be configured with smart tags. Though a CT system is described by way of example, it should be understood that the present techniques may also be useful when applied to other assets, such as magnetic resonance imaging (MRI) systems, ultrasound scanners, catheterization lab equipment, gas analyzers (such as chromatography systems), photocopiers, surgical tool kits, and so forth. The present discussion of a CT imaging modality is provided as an example of one suitable asset.

FIG. 1 illustrates an exemplary CT system 100. Particularly, the CT system 100 is configured to image a subject (not shown in FIG. 1) such as a patient, an inanimate object, one or more manufactured parts, and/or foreign objects such as dental implants, stents, and/or contrast agents present within the body. In one embodiment, the CT system 100 includes a stationary housing 10 that houses a gantry 102, which in turn, may further include at least one x-ray radiation source 104 configured to project a beam of x-ray radiation 106 for use in imaging the subject. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the subject at different energy levels.

In certain embodiments, the CT system 100 further includes an image processor unit 111 configured to reconstruct images of a target volume of the subject 112 using an iterative or analytic image reconstruction method. For example, the image processor unit 111 may use an analytic image reconstruction approach such as filtered backprojection (FBP) to reconstruct images of a target volume of the patient. As another example, the image processor unit 111 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector.

In an axial scan, the projection data is processed to reconstruct an image that corresponds to a two-dimensional slice taken through the object. To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

FIG. 2 illustrates an exemplary imaging system 200 similar to the CT system 100 of FIG. 1. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device such as mass storage 218. The mass storage 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction.

The various methods and processes described further herein may be stored as executable instructions in non-transitory memory on a computing device in imaging system 200. For example, computing device 216 may include instructions in non-transitory memory, and may apply the methods described herein, at least in part, receive notifications from one or more smart tags and output the notifications to an operator or send the notifications to an external monitoring device, such as via a "cloud" network cluster.

One or more components of the CT system may include associated smart tags. As shown in FIG. 1, CT system 100 includes a plurality of smart tags, including smart tag 110 and smart tag 120. Smart tag 110 may be coupled to and associated with gantry 102, while smart tag 120 may be coupled to and associated with stationary housing 10. Other components of CT system 100 may likewise include smart tags coupled thereto, including but not limited to components of radiation source 104, radiation detector 108, table 228, etc.

As will be described in more detail below, the smart tags (e.g., tags 110 and 120) may broadcast tag information that may be received by other smart tags within proximity of the smart tags. The tag information may include information to uniquely identify that tag, as well as associate that tag as part of one or more families. When two or more smart tags in proximity of each other include matching family information, those smart tags may "dynamically swarm" into a family, whereby each smart tag of the family in proximity learns of the other smart tags of that family in proximity. The smarts tags may then track how many smart tags are in the family and issue notifications once the number of smart tags changes. Further, the smart tags may assess additional attribute information of the smart tags in proximity, where the attribute information may verify the origin of the part to which the smart tag is associated. For example, if a smart tag in proximity broadcasts attribute information that indicates the smart tag is associated with a part that is not approved to be included in the CT imaging system (e.g., a non-original manufacturer part or an expired part), the smart tags in proximity may issue notifications indicating that a non-approved part has been placed in the CT imaging system. The notifications may be received by other smart tags and/or one or more listeners in proximity. In this way, changes to parts within the CT imaging system may be tracked in real-time using a decentralized, smart tag system.

The CT system may be installed in a hospital or other clinical setting, and may be serviced (e.g., routine maintenance or due to degraded components) on-site by a field engineer (at the hospital or other clinical setting). During service, worn or degraded parts may be replaced by the field engineer. To perform an on-site service, the field engineer may bring a tool kit, which may include replacement parts and tools for performing the service. An example tool kit 150 is shown in FIG. 1. Tool kit 150 may include a plurality of replacement parts 152. The replacement parts may include coils, sensors, batteries, motors, or virtually any field-replaceable part that may be installed in a CT system. The plurality of replacement parts 152 may include multiple redundant parts (e.g., two or more of the same sensor) and/or one of a given part type. Tool kit 150 may further include a plurality of tools 154. The plurality of tools may include hammers, screwdrivers, drills, or any suitable tool that may be used to service CT system.

Each tool or replacement part in the tool kit 150 may include a smart tag coupled thereto, such as smart tag 156. As described above, each smart tag may include (and broadcast) attribute and family information that identifies a corresponding part to which the smart tag is attached, one or more families to which the corresponding part belongs, and additional information. As an example, each replacement part of the plurality of replacement parts 152 may include a smart tag, and each of those smart tags may associate as a family (e.g., a family of CT system replacement sensors). If a first replacement part from the family is removed and installed in CT system 100, the smart tags associated with the other replacement parts remaining in tool kit 150 may detect that the first replacement part has been moved out of proximity of the tool kit (based on dissociating from the smart tag of the first replacement part). The smart tags of the remaining replacement parts may determine that the remaining replacement part inventory in tool kit is low (e.g., below a threshold) and broadcast a notification that a new replacement part should be placed into tool kit 150. Once the first replacement part is installed in the CT system, the smart tag of the first replacement part may associate with other smart tags of the CT system (e.g., tags 110 and 120).

Figure 3:
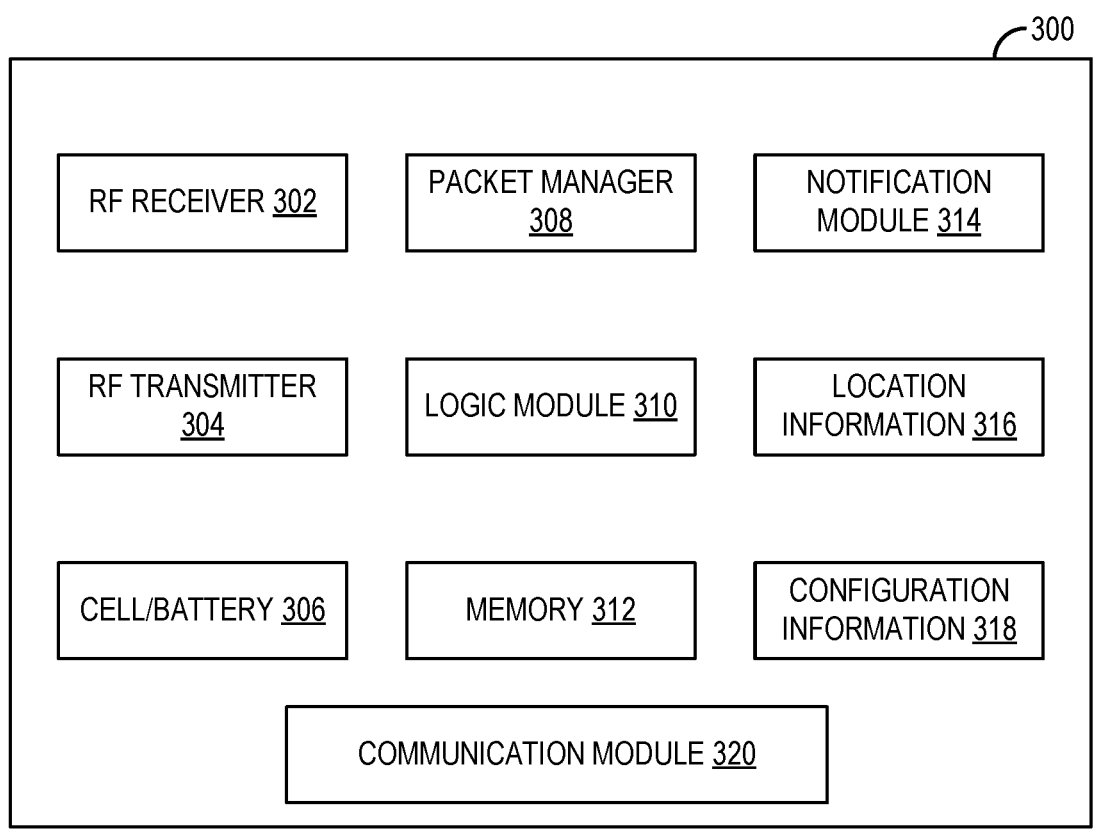
FIG. 3 is a block diagram illustrating an example smart tag.

FIG. 3 is a block diagram of an example smart tag 300. Smart tag 300 is a non-limiting example of smart tag 110, smart tag 120, and smart tag 156 and may be associated with (e.g., coupled to) virtually any suitable physical part or component. Smart tag 300 may be an application-system integrated circuit (ASIC) including one or more microprocessors, memory blocks, and other hardware. However, in other examples smart tag 300 may be field programmable gate array or other logic unit.

Smart tag 300 includes a radio frequency (RF) receiver 302, an RF transmitter 304, and an energy cell and/or battery 306. In examples where smart tag 300 includes an energy cell, smart tag 300 may be powered via solar energy. RF receiver 302 may receive RF signals (e.g., from other smart tags). The received RF signals may be converted into custom packets by a packet manager 308. Packet manager 308 may convert RF signals into suitable packets, such as extensible markup language (XML) packets. Packet manager 308 may also convert the custom packets to RF signals that may be transmitted (e.g., to other smart tags) via RF transmitter 304.

The custom packets may be received by logic module 310. Logic module 310 may parse the received packets and/or otherwise process the information in the received packets in order to determine how the received packets are to be handled by the smart tag. For example, if the received packets include family or attribute information of a newly-discovered smart tag, logic module 310 may identify the family information and store that tag's family information in memory. The memory may be associated with logic module 310, or the memory may be a separate memory 312. Memory 312 may include ROM, RAM, EEPROM, flash memory, or other suitable memory.

Memory 312 (or a separate memory block) may store configuration information 318 for smart tag 300. Configuration information 318 may include a unique identifier for smart tag 300, one or more family identifiers (e.g., classifying that smart tag as a member of a tool kit, a particular imaging system, and/or other family), attribute information (which may indicate information regarding the part to which smart tag 300 is coupled, such as manufacturer), threshold information (e.g., how many members of the family to which smart tag 300 belongs are needed, below which a notification may be issued), and other information. Memory 312 may store location information 316. Location information 316 may include a current location of smart tag 300 and a previous location of smart tag 300. In examples where smart tag 300 does not include location service capabilities, the current and previous location of the smart tag may be based on attribute information as well as a current family identification. For example, the family identification may indicate the smart tag is currently a member of a CT imaging system family while a prior family identification may indicate the smart tag was previously a member of a tool kit replacement part family. The attribute information may specify that smart tag is to be placed into a particular CT imaging system at a known hospital, for example.

Logic module 310 may determine, from the received packets, if a notification is to be issued. As mentioned previously, logic module 310 may receive packets from all smart tags in proximity to smart tag 300 (as used herein, "in proximity" includes in communication with, which will be described in more detail below). Logic module 310 may retrieve identification information (such as family identification, security information, and other attribute information) from the received packets. If the identification information indicates that another smart tag in proximity is to be included in the same family as smart tag 300, logic module 310 stores the identification information for the other smart tag in memory. In response, logic module 310 may command an acknowledgement be sent to the other smart tag, including identification information for smart tag 300. Logic module 310 may inform notification module 314 to send a notification including the acknowledgement and identification information. Notification module 314 may then select or generate the proper notification, packet manager 308 may covert the notification packets to an RF signal, and RF transmitter 304 may transmit the RF signal. Any smart tags in proximity may receive the transmitted RF signals. In this way, a plurality of smart tags in communicative proximity with each other may each store information identifying the other proximate smart tags.

Additional notifications may be sent in a similar manner. Other notifications may include an inventory alert notification that may be broadcast responsive to logic module 310 determining that the number of smart tags of a given family in proximity to smart tag 300 has dropped below a threshold number. For example, logic module 310 may update a counter for a first family (stored in logic module 310 or in memory 312) each time a new smart tag in the first family is identified (e.g., increase the value of the counter by one). When a smart tag in the first family is dissociated from the family (e.g., moved out of proximity), logic module 310 may update the counter (e.g., decrease the value of the counter by one). If the counter reaches a threshold specified in the configuration information 318, a notification may be broadcast indicating the first family is below the threshold number of family members. Further notifications may include conflicting attribute information notifications (e.g., if a smart tag is detected that has non-approved or non-matching attribute information), battery life notifications, or other notifications.

Smart tag 300 may further include a communication module 320. Communication module 320 may be configured to communicate with other smart tags and/or listeners via a suitable communication protocol, such as near field communication or low-energy BLUETOOTH®. In some examples, RF receiver 302 and RF transmitter 304 may be tuned to send/receive RF signals according to a near field communication or low-energy BLUETOOTH® protocol, and as such a separate communication module 320 may be omitted. In other examples, communication module 320 may include a separate antenna from RF receiver 302 and RF transmitter 304. In still further examples, additionally or alternatively, communication module 320 may be configured to communicate notifications and/or other information over Wi-Fi, e.g., to the cloud or an Internet-enabled device (such as a computing system). Communication module 320 and/or RF receiver 302 and RF transmitter 304 may be configured to send and receive signals that are broadcast a relatively short distance (e.g., one meter, ten meters). Once a smart tag is moved out of communication range of communication module 320 and/or RF receiver 302 and RF transmitter 304, that smart tag may be considered to be out of proximity of smart tag 300. Once a smart tag is moved into of communication range of communication module 320 and/or RF receiver 302 and RF transmitter 304, that smart tag may be considered to be within proximity of smart tag 300.

Thus, smart tag 300 includes a communication system to send and receive packets that include identification information. The identification information is usable by smart tag 300 and other smart tags in proximity to dynamically associate the smart tags into a family, for example based on the smart tags being in proximity to one another and further based on broadcast identification information matching stored identification information (e.g., if identification information broadcast by a first smart tag matches identification information stored in memory of a second smart tag, such as smart tag 300, the first and second smart tags may associate as a family). The identification information stored in memory for the first smart tag may include suitable information that uniquely characterizes the first smart tag by identification, features, attributes, and associations; other smart tags may likewise be uniquely characterized by their respective stored identification information. This identification information may be broadcast at regular intervals (e.g., every minute, every hour, or other suitable frequency) such that other smart tags in proximity may confirm whether or not the number of members in the family has changed.

In one example, the identification information that is broadcast may include, for smart tag 300 and other smart tags, a header, a secure code, a checksum, a tag identification, a dynamic family identification, tag attributes, a count of members in the dynamic family, and a family association. The secure code is configured at smart tag installation and/or deployment and is configured for a specific deployment such as field engineer tool kit (e.g., a code for the field engineer and a code for the specific tool kit). The secure tag may define the smart tag as a valid tag and hence confirm that a third-party part or other non-accepted part is not being used. All tags belonging to the field engineer tool kit would validate each other not only by the common family identification but also by the secure code. The tag identification may uniquely identify that smart tag. The family identification may associate the smart tag to an existing family. Each smart tag in a family would share the same family identification. The family identification may be auto-generated each time a new family is formed (e.g., when smart tag 300 first associates as belonging to a family by being brought into proximity of another smart tag and confirming that identification information received from that smart tag matches identification of smart tag 300). In other examples, the family identification may be pre-configured based on system constraints, goals, or other parameters (e.g., that dictate what level of uniqueness of the identification is needed). The tag attributes may provide context to the smart tag on how the smart tag is being used, where it is deployed (e.g., in an aisle, within an imaging system, on a peripheral device), how the tag can be discovered, and other metadata that helps drive analytics and service for a particular tag. Thus, the tag attributes may include information about the smart tag and component to which the smart tag is coupled, including type of tag, deployment context (such as field engineer inventory, imaging bill of materials, customer inventory, point of sales display, and so forth), manufacturer of the part, date of part deployment, etc. The family association may be a binary indicator where 1 indicates the smart tag is currently a member of a family and 0 indicates the smart tag is not currently a member of a family. In this way, as each smart tag moves into and out of a given family, the smart tag is marked as an individual or family member. Each smart tag broadcasts the RF signal with the identification information described above, and each smart tag that receives the identification information has a packet manager to translate the signal and parse the payload to initiate dynamic swarming and associated notifications.

Figure 4:
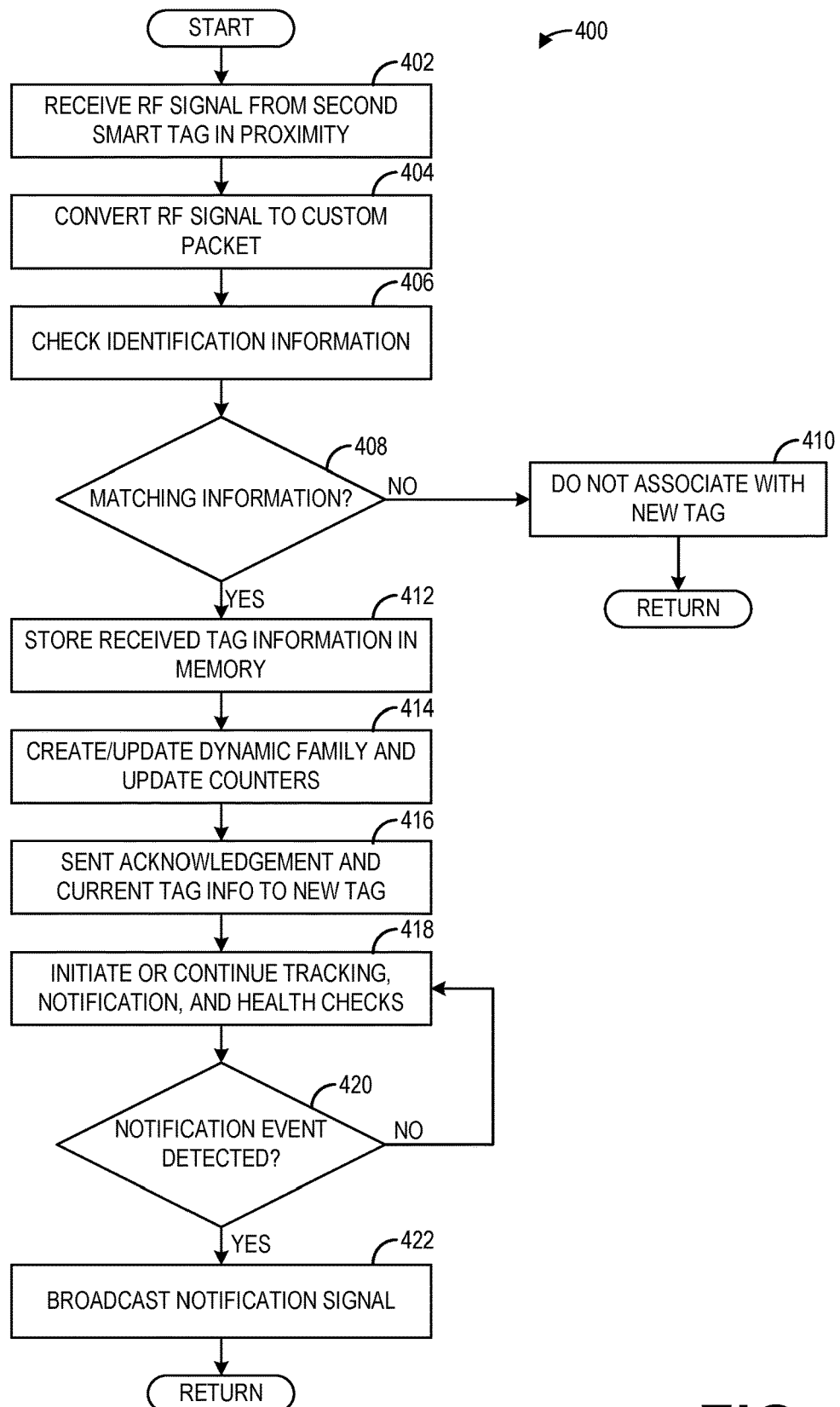
FIG. 4 is a flow chart illustrating a method for dynamically associating a family of smart tags.

Turning to FIG. 4, a method 400 for operating a smart tag is shown. Method 400 is described with regard to the systems and components depicted in FIGS. 1-3, though it should be appreciated that the method may be implemented with other systems and/or components without departing from the scope of the present disclosure. Method 400 may be implemented as executable instructions in non-transitory memory of a device, such as smart tag 300. Method 400 presents an example routine that smart tag 300 may execute in response to detecting a new smart tag. In the description of method 400, the smart tag executing the method (e.g., smart tag 300) may be referred to as the first smart tag. The new smart tag may be a smart tag that has not yet been identified by the first smart tag, and may be referred to as the second smart tag.

At 402, method 400 includes receiving an RF signal from a second smart tag in proximity to the first smart tag. The RF signal may be received at an RF receiver of the first smart tag in response to the second smart tag being moved into proximity with the first smart tag for the first time. At 404, method 400 includes converting the received RF signal to one or more a custom packets. For example, the RF signal may be converted to XML packets at a packet manager of the first smart tag. At 406, method 400 includes checking the identification information (e.g., the secure code, family identification, and/or other attributes) of the second smart tag. The first smart tag may parse the custom packet(s) (e.g., with a logic module) to determine the identification information of the second smart tag, including the secure code and family identification as well as other information relating to the second smart tag (e.g., attributes).

At 408, method 400 determines if the identification information of the second smart tag matches identification information of the first smart tag. For example, the first smart tag may store configuration information of the first smart tag that includes the family identification(s) to which the first smart tag belongs. The logic module of the first smart tag may compare the family identification(s) of the second smart tag to the family identification(s) of the first smart tag and if at least one of the family identifications match, the first smart tag may determine that the first smart tag and the second smart tag belong to the same family. In another example, additionally or alternatively, the configuration information of the first smart tag may include a first secure code that identifies the intended deployment of the part to which the first tag is coupled (e.g., tool kit, CT imaging system). The logic module of the first smart tag may compare a second secure code of the second smart tag to the first secure code of the first smart tag, and if the secure codes match (or indicate the smart tags are both valid, have the same deployment, or other matching characteristic), the first smart tag may determine that first smart tag and second smart tag belong to the same family.

If it is determined that the identification information does not match (e.g., if the first smart tag and second smart tag do not belong to the same family), method 400 proceeds to 410 and the first smart tag does not associate with the second smart tag. In this way, the dynamic association of tags based on proximity is not initiated when the identification information does not match. For example, an operator, field engineer, or other user may try to replace an authenticated original manufacturer (OEM) part having a valid smart tag with a non-OEM part. The removal of the OEM part is recognized by smart tags within that family but the installation of the new part cannot be tracked due to the new part not including a valid smart tag (e.g., based on the secure code of the smart tag, or based on the part not even having a smart tag). The smart tags in proximity (e.g., the first smart tag) may output a notification of a non-matching smart tag in proximity, or a listening device may determine the first and second smart tags have not swarmed into a family. Another example is when non-matching parts or assets are placed at a particular location either by accident or intentionally. For example, surgical tool kits for a first type of procedure may be stored in a particular location in a hospital. If a clinician or other user accidentally leaves a surgical tool kit for a different, second type of procedure with the surgical tool kits for the first type of procedure, the smart tags of the different surgical kits may recognize that one of the surgical tool kits has been left in the wrong location and output a suitable notification. Method 400 then returns.

If it is determined that the identification information does match (e.g., if the first smart tag and second smart tag do belong to the same family), method 400 proceeds to 412 to store the received second tag information in memory of the first smart tag. The family identification of the second smart tag, as well as other information of the second smart tag (e.g., attributes, secure code, and tag ID number) may be stored in memory of the first smart tag in addition to the identification information of the first smart tag. At 414, method 400 includes creating and/or updating a dynamic family (also referred to as a dynamic swarm) and updating any relevant counters. The first and second smart tags may associate as a family. Any other members of that family already identified by the first smart tag are also included in the family. The relevant counters may include a family number counter, where the number of members in that family (determined by the first smart tag and stored in memory) may be incremented by one in response to determining the first smart tag and the second smart tag belong to the same family.

At 416, method 400 sends an acknowledgement notification that includes information pertaining to the first smart tag, such as attributes, family identification(s), and other information of the first smart tag. This notification may be sent to the second smart tag (and any other tags in proximity). To send the notification, the first smart tag may generate or retrieve the notification via the notification module, covert the notification to RF signals at the packet manager, and then send the RF signals via the RF transmitter.

At 418, method 400 initiates or continues tracking, notification, and/or health checks. For example, the first smart tag may continue to receive RF signals from other smart tags in proximity. Each time an RF signal is received, the first smart tag may parse the received packets to determine which smart tag sent the signals. If the smart tag that send the signals is a new smart tag (e.g., not previously identified), the first smart tag may execute method 400 again to establish communication and/or dynamically swarm with the new smart tag. If the smart tag that sent the signals is not new (e.g., first smart tag is already in a family with that smart tag), the first smart tag may determine if any new information is being sent by that smart tag, and if so, update the information stored for that smart tag. In some examples, the first smart tag may regularly broadcast a status notification to notify the other family members that the first smart tag is still in proximity. Likewise, the first smart tag may receive status notifications from the other smart tags in proximity. If a predetermined duration has elapsed since receiving a status notification from another smart tag in the family, the first smart tag may determine that the other smart tag has been dissociated from the family. The first smart tag may then update the counter to reflect that the other smart tag is no longer being in the family. If the counter reaches a threshold, the first smart tag may then broadcast a notification indicating low inventory for the family. Further, the first smart tag may assess the life of its battery and may broadcast a notification when its battery life is below a threshold.

At 420, method 400 includes determining if a notification event is detected. As explained above, the first smart tag may broadcast notifications for a variety of reasons (e.g., status update, low inventory, battery life). If no notifications are to be sent, method 400 returns to 418 to continue monitoring for notifications. If a notification is to be sent, method 400 proceeds to 422 to broadcast the notification (e.g., as RF signals). Method 400 then returns.

Figure 5:
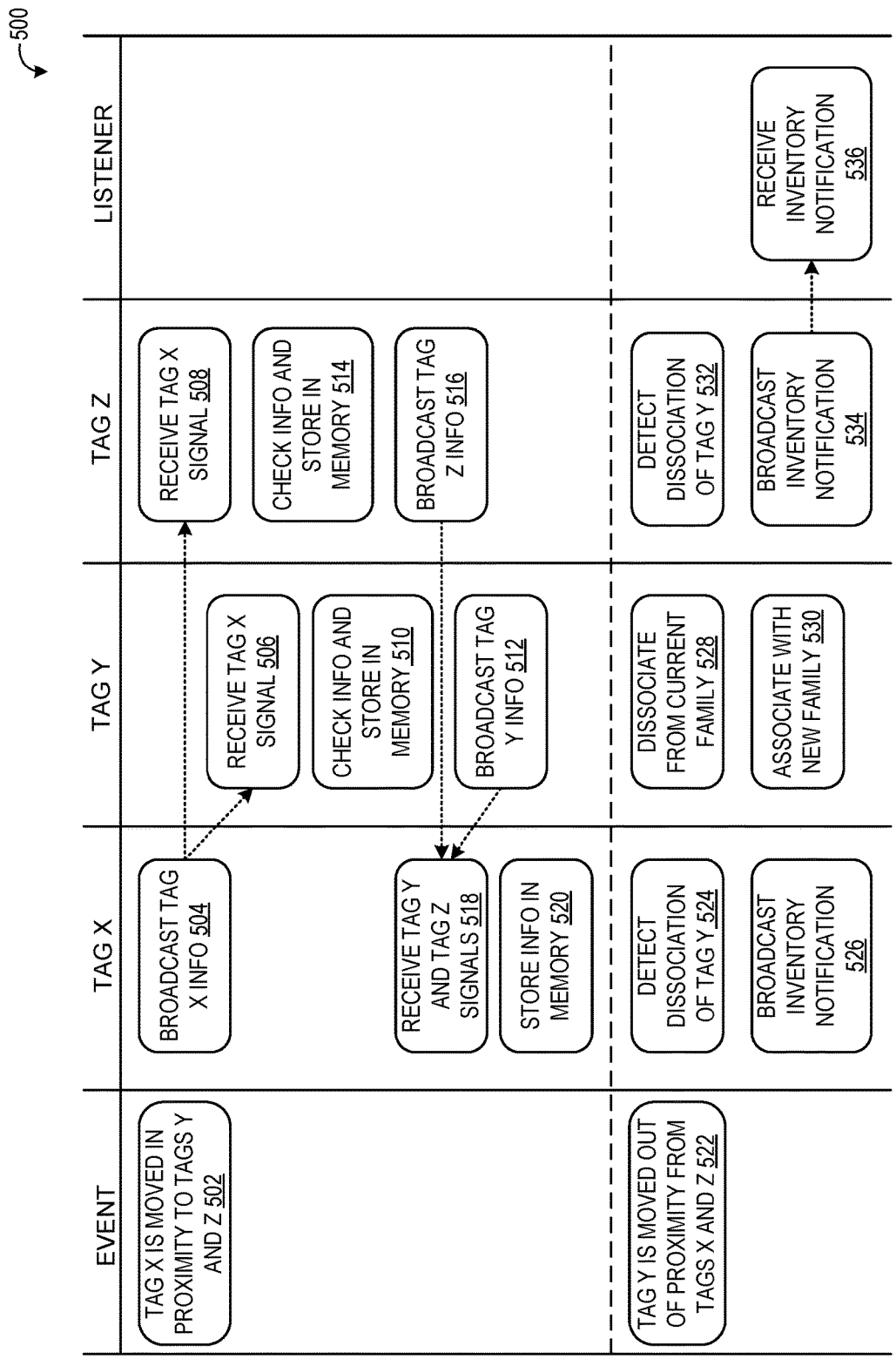
FIG. 5 is a block communication diagram illustrating a flow of information during a dynamic family association and dynamic family dissociation.

FIG. 5 is a block communication diagram 500 that schematically shows example communication among a plurality of smart tags, such as smart tag 300 and other smart tags. Communication diagram 500 includes triggering events (the leftmost panel of FIG. 5), events and communication of a first smart tag (tag x), events and communication of a second smart tag (tag y), events and communication of a third smart tag (tag z), and events of a listener (the rightmost panel). The listener may be an RF reader brought into proximity of the smart tags, a computing device in proximity of the smart tags, or other suitable device configured to receive and parse communication from the smart tags in order to communicate various notifications to a user. For example, NFC/BTE may be used to communicate with a server through smart devices (e.g., smart phones, edge devices) that are close to the smart tags, or through WI-FI or RF, and/or through wall- or ceiling-mounted devices in the facility where the smart tags are deployed. In the example of a surgery room, a ceiling-mounted listener or a listener built into an existing location tracking receiver may be used to send the received notifications to a central server, and additional capability may be implemented to push the notifications directly to a clinical smart phone that is configured to receive and/or parse the notifications for real time mitigation. In the second case, the tags are directly broadcasting notifications that are captured by the smart phone through BTE, NFC, or WI-FI.

A first trigger event includes tag x being moved into proximity of tags y and z, as indicated at 502. Tag x broadcasts identification information for tag x, at 504. At 506, tag y receives the identification information from tag x, and at 508, tag z also receives the identification information from tag x. At 510, tag y checks the received information from tag x and determines that tag x belongs to the same family as tag y. Thus, tag y also stores the identification information from tag x in memory. In response, tag y broadcasts an acknowledgement notification at 512 that includes identification information for tag y. Likewise, at 514, tag z checks the received information from tag x and determines that tag x belongs to the same family as tag z. Thus, tag z also stores the identification information from tag x in memory. In response, tag z broadcasts an acknowledgement notification at 516 that includes identification information for tag z.

As shown at 518, tag x receives the signals sent by tag y and tag z, and at 520, tag x stores the identification information sent by tag y and by tag z in memory. In this way, each of tag x, tag y, and tag z may establish communication with one another and determine that each of the tags belongs to the same family. Upon determining that the tags are all in the same family, each tag may update their respective counter and family association information to reflect the formation of the family, and send their own identification information out to the other tags, while storing the identification for the other tags in the family. While not shown in FIG. 5, tag y receives and stores identification information from tag z, and tag z receives and stores identification information from tag y.

At a subsequent time, tag y is moved out of proximity from tags x and z, as shown at 522. At 524, tag x detects dissociation of tag y from the family. Tag x may detect the dissociation responsive to a threshold amount of time having elapsed since receiving a status notification from tag y. In the example shown in FIG. 5, the counter stored in memory of tag x may indicate that the number of members within the family has dropped below a threshold, due to tag y being dissociated. In response, tag x may broadcast an inventory notification at 526. The inventory notification may include that the family has low inventory. Likewise, at 532, tag z detects dissociation of tag y from the family and broadcasts an inventory notification at 534.

Tag y detects that it has dissociated from the family at 528. Tag y may determine that it has dissociated from the family in response to a threshold amount of time having elapsed since receiving status notifications from the other members of the family (e.g., from tags z and z), due to being moved out of communicative proximity from the other family members. In some examples, tag y may only be dissociated upon being moved out of proximity of all tags within its family. For example, tag y may be moved out of proximity of tag x, but may remain in the family until tag y is also moved out of proximity of tag z. Upon being dissociated from the family, tag y may update its family association to reflect that tag y is no longer associated with a family. Tag y may continue to broadcast its identification information, and if tag y is moved into proximity of a new family, tag y may associate with the new family, as shown at 530. The association with the new family may only occur if the identification information broadcast by tag y (e.g., secure code and/or family identification) matches identification information stored by other tags in proximity to tag y.

In some examples, a listener may be present in proximity to tags x and z. For example, a field engineer may have a reader/scanner that is configured to communicate with (or at least receive broadcast notifications from) smart tags in proximity. In other examples, a computing device (e.g., a computing device/controller of a medical imaging system such as computing device 216 of FIG. 2) in proximity of tags x and z may be configured to receive notifications from tags x and z. In such examples, the listener may receive one or both of the inventory notifications broadcast by tags x and z. As shown, the listener receives the inventory notification broadcast by tag z at 536. In response, the listener may output the notification in such a manner that an operator may be notified of the low inventory. In one example, tags x and z may be members of a field engineer tool kit, and the operator may be notified of the low inventory so that the operator may restock the tool kit with the appropriate tool or replacement part. For example, tag y may be coupled to a replaceable part of a CT imaging system, such as a balance sensor. During service of the CT imaging system, the balance sensor in the CT imaging system may be replaced by the balance sensor (to which tag y is associated) in the tool kit. Thus, tag y moves out of the tool kit and dissociates from the tool kit family. This prompts the inventory notification from tags x and z, which remain in the tool kit. The operator may then add a new balance sensor to the tool kit to maintain desired supply of the balance sensor in the tool kit.

In another example, tags x and z may be members of a CT imaging system family, where tags x and z are coupled to respective components of a CT imaging system (such as tags 110 and 120 of FIG. 1). Tag y may be coupled to a replaceable component of the CT imaging system, such as a balance sensor. During service of the CT imaging system, the balance sensor (and associated tag y) may be removed from the CT imaging system, prompting dissociation of tag y from the CT imaging family. The listener may receive the subsequent inventory notifications from tags x and z and output the notifications to an operator, such as the field engineer or to a manager or other remote operator. If a new balance sensor (with an associated new smart tag) is not placed into the CT imaging system family within a threshold amount of time, the operator may assume that the CT imaging system is not in service (e.g., the field engineer was unable to install a new balance sensor), or the operator may assume that a non-approved balance sensor was installed in the CT imaging system, such as a balance sensor manufactured by a third party (e.g., a non-OEM part). If tags x and/or z begin to issue non-matching attribute notifications, this may further indicate a non-approved part was installed in the CT imaging system. For example, the new balance sensor may have a smart tag to which tags x and z may communicate, but the attribute information broadcast by the new smart tag may not match the attribute information stored by tags x and z. In either case, installation of a non-approved part may cause termination of a warranty agreement, prompt a follow-up service, or cause another action.

A technical effect of the smart tags disclosed herein provide is dynamic, ad-hoc family formation not managed by a central computing device. Another technical effect is simplified, decentralized inventory management that may be applied in many different settings. As an example, the smart tags disclosed herein may provide for active asset management and utilization through the self-monitoring family of assets that leverage the dynamic swarming smart tags. Advanced workflows such as asset transfers/sale/rentals, transport, etc., may be configured based on the dynamic swarming of smart tags and the related events may be integrated into an asset performance management framework.

As another example, the smart tags may facilitate inventory management, where self-managed inventory and periodic automatic replenishment (PAR) level maintenance may be built using dynamic swarming tags, where the tags may keep a count of inventory in a given family and initiate part requisition workflows when the counter reaches a threshold. No external integrations to manage inventory are needed since the dynamic swarm would detect the current state of the associated family inventory automatically.

As an example, the smart tags may facilitate part configuration monitoring and warranty/contract compliance management. Using the dynamic swarming smart tags, the BOM associated to a customer asset (e.g., medical imaging system) under warranty or contract may be closely managed and any changes to the part configuration resulting from part replacements with unapproved parts may be easily detected since the dynamic swarming tags are self-managing and aware.

Another example includes tool kit management. As explained above, field engineers typically carry a limited amount of FRUs and tools with them to ensure timely service intervention and to avoid unnecessary wait times. The challenge is to track inventory of parts and tools that each field engineer may have at any given time. This can be easily tracked and self-managed using the dynamic swarming smart tags.

Another example includes mobile truck tool inventory. Field trucks and mobile trucks carrying equipment such as scanners typically have tools anchored in the truck. To ensure that the tools being kept on these trucks are always ready and available, it is important to have a system that can detect the integrity of all the tools at all times. The use of dynamic swarming tags not only facilitates the tracking of the count of tools at any given time, but it also detects movement of tools outside of the anchored/allocated locations.

As a further example, the smart tags disclosed herein may be used in a surgical kit in an operating room, an EMT kit, or any other use case that requires a set of assets to be available as part of a group and in specific location/order. Ordering of parts within an asset such as a tool kit may be enforced through the use of tag attributes and additional logic. For example, the tag attributes may include an order attribute. By setting the order attribute on each tag when each tag becomes part of a family or disassociates itself from the family, the events being generated may be mapped to the order being set to ensure everything is done as planned. For example, the defined order of a surgical kit may include a surgical knife that is to be placed right after a tool that helps prepare the surgical area, and a stitching tool is to be placed right after the surgical knife. In this case, the ordering may be stitching tool, surgical knife, and preparation tool. If the tools are placed on the table in a different order, a notification may be sent with alerting a listener that the tools have been placed on the table in the wrong order. Another example includes patient flow and asset flow in a hospital environment that may be managed using dynamic smart tags as the tags provide a mechanism to notify where a patient or asset is located by associating the tags (which may be coupled to the patient or asset, where the asset may include a mobile IV unit or other mobile medical device) to a family such as a hospital bed or room. As the patient or asset being tracked through the dynamic smart tags moves from place to place, events are broadcasted indicating tags leaving one family and entering another. Through this event data and integrating that to the clinical and patient work flows would help manage the overall flow.

A further example where the smart tags disclosed herein may be utilized includes treatment management and compliance (e.g., JCAHO), which may be monitored using the smart tags. Dynamic swarming tags may help identify how a given patient being admitted with a specific ICD code is being taken care of by keeping track of medical equipment, room categories, clinicians, doctors, and workflow as the dynamic association of patient to any combination of these is tracked through events. For example, every time a patient with the dynamic tag is in the proximity of a tagged medical equipment and clinician in a specific room, this may result in one dynamic family. If anything changes to this setup, new events are triggered as the dynamic family gets updated and corresponding event notifications are published.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a plurality of smart tags each configured to be coupled to a respective component of a medical imaging system, each smart tag of the plurality of smart tags configured to broadcast identification information usable by other smart tags in order to dynamically form a family, the family formed based on the broadcast identification information matching stored identification information and further based on a proximity of each smart tag of the plurality of smart tags to one another.

2. The system of claim 1, wherein the medical imaging system comprises a computed tomography (CT) imaging system including a plurality of components, each component including a smart tag of the plurality of smart tags.

3. The system of claim 2, wherein each of the plurality of smart tags is configured to broadcast identification information that includes a secure code that indicates an intended deployment for the component to which that smart tag is coupled.

4. The system of claim 2, wherein each of the plurality of smart tags is configured to broadcast identification information that includes a family identification identifying the family to which that smart tag belongs.

5. The system of claim 1, wherein the family being formed based on the broadcast identification information matching stored identification information includes, for a first smart tag and a second smart tag of the plurality of smart tags:
the first smart tag broadcasting first identification information, the first identification information stored in memory of the first smart tag;
the second smart tag receiving the first identification information and comparing the first identification information to second identification information, the second identification information stored in memory of the second smart tag; and
the first smart tag and the second smart tag forming the family in response to the first identification information matching the second identification information.

6. The system of claim 5, wherein the family being formed further based on the proximity of each smart tag of the plurality of smart tags to one another includes, for the first smart tag and the second smart tag, the second smart tag only receiving the first identification information when the second smart tag is within a threshold distance of the first smart tag.

7. The system of claim 1, wherein the plurality of smart tags is a first plurality of smart tags and the family is a first family, and further comprising a second plurality of smart tags each configured to be coupled to a respective replacement part of a field engineer tool kit, each replacement part configured to replace a corresponding component of the medical imaging system, and wherein each smart tag of the second plurality of smart tags is configured to broadcast second identification information usable by other smart tags in order to dynamically form a second family, the second family formed based on the broadcast second identification information matching stored second identification information and further based on a proximity of each smart tag of the second plurality of smart tags to one another.

8. A smart tag, comprising:
a communication system configured to receive and broadcast notifications;
a storage system storing a first family classification for the smart tag, the first family classification indicating that the smart tag is a first member of a first family; and
a logic system configured to:
determine, based on one or more notifications received via the communication system, that at least one second member of the first family has been moved out of proximity of the smart tag;
update a counter to reflect that the at least one second member has left the first family; and
determine that the counter has dropped below a threshold and in response, broadcast a notification indicating the first family has low inventory.

9. The smart tag of claim 8, wherein the logic system is configured to determine that the at least one second member has been moved out of proximity of the smart tag by:
establishing that the at least one second member is part of the first family based on notifications received from one or more respective smart tags associated with the at least one second member;
determining that a plurality of status notifications from the one or more respective smart tags has been received at the communications system, each status notification received at a predetermined time interval; and
indicating that the at least one second member has been moved out of proximity of the smart tag in response to a threshold duration elapsing since a previous status notification was received.

10. The smart tag of claim 8, wherein the logic system is further configured to:
identify, in a first notification received at the communication system, a second family classification for another smart tag in proximity with the smart tag;
determine that the first family classification matches the second family classification and, in response, add the other smart tag as a member of the first family;
based on the determination, store the second family classification in the storage system and broadcast a second notification via the communication system, the second notification including the first family classification; and
update the counter to reflect that the other smart tag has joined to the first family.

11. The smart tag of claim 8, wherein the smart tag is coupled to a component of a medical imaging system, and wherein the first family comprises a plurality of additional smart tags each coupled to a respective additional component of the medical imaging system.

12. The smart tag of claim 8, wherein the smart tag is coupled to a replaceable part of a medical imaging system, the replaceable part housed in a tool kit, and wherein the first family comprises a plurality of additional smart tags each coupled to a respective additional replaceable part of the medical imaging system housed in the tool kit.

13. The smart tag of claim 8, wherein the storage system stores first attribute information for the smart tag, and wherein the logic system is further configured to:
identify, in a first notification received at the communication system, second attribute information for another smart tag in proximity with the smart tag;
determine that the first attribute information does not match the second attribute information and, in response, broadcast a second notification via the communication system indicating the second attribute information does not match the first attribute information.

14. The smart tag of claim 13, wherein the first attribute information identifies a manufacturer of a first component to which the smart tag is coupled, and the second attribute information identifies a manufacturer of a second component to which the other smart tag is coupled.

15. The smart tag of claim 8, wherein the communication system comprises a radio frequency (RF) receiver and an RF transmitter.

16. A method for a plurality of smart tags, each smart tag of the plurality of smart tags coupled to a respective physical component, the method comprising:
dynamically associating the plurality of smart tags into a family responsive to the plurality of smart tags being brought into proximity of one another, and further responsive to each smart tag broadcasting identification information that matches identification information stored by the other smart tags, wherein any smart tags that broadcast identification information that does not match the identification information stored by the other smart tags are not included in the family; and
dissociating a first smart tag of the plurality of smart tags from the family responsive to the first smart tag being moved out of proximity of the other smart tags.

17. The method of claim 16, wherein dynamically associating the plurality of smart tags into the family responsive to the plurality of smart tags being brought into proximity of one another, and further responsive to each smart tag broadcasting identification information that matches identification information stored by the other smart tags comprises, for each smart tag:
  broadcasting first identification information for that smart tag;
  receiving second identification information for each other smart tag, each second identification information sent from a respective other smart tag and only received by that smart tag when that smart tag is within a threshold distance of the other smart tags;
  determining that the first identification information matches the second identification information and, in response, associating that smart tag with the other smart tags in the family.

18. The method of claim 16, further comprising upon dissociating the first smart tag of the plurality of smart tags from the family, updating a counter on each remaining smart tag that tracks a number of members of the family to reflect that the first smart tag has dissociated from the family.

19. The method of claim 18, further comprising broadcasting a notification, from each communication system of each smart tag, indicating the family has low inventory.

20. The method of claim 19, wherein broadcasting the notification from each communication system of each smart tag includes broadcasting the notification from each radiofrequency transmitter of each smart tag.

* * * * *